United States Patent [19]
Mohr et al.

[11] Patent Number: 6,039,864
[45] Date of Patent: *Mar. 21, 2000

[54] HYDROCARBON CONVERSION PROCESS USING A ZEOLITE BOUND ZEOLITE CATALYST

[75] Inventors: Gary David Mohr, League City, Tex.; Johannes Petrus Verduijn, Bertem, Belgium

[73] Assignee: Exxon Chemical Patents Inc., Houston, Tex.

[*] Notice: This patent is subject to a terminal disclaimer.

[21] Appl. No.: 09/081,340

[22] Filed: May 19, 1998

Related U.S. Application Data

[60] Division of application No. 08/561,674, Nov. 22, 1995, Pat. No. 5,993,642, which is a continuation-in-part of application No. 08/344,034, Nov. 23, 1994, abandoned.

[51] Int. Cl.⁷ ..................................................... C10C 5/52
[52] U.S. Cl. .................. 208/134; 208/135; 208/146; 585/470; 585/475; 585/481
[58] Field of Search .................................. 208/134, 135; 585/470, 475, 481

[56] References Cited

U.S. PATENT DOCUMENTS

| | | | |
|---|---|---|---|
| 3,356,450 | 12/1967 | Heinze ....................................... | 23/112 |
| 3,781,226 | 12/1973 | Schwartz ............................. | 252/455 Z |
| 4,091,007 | 5/1978 | Dwyer et al. ........................... | 260/448 |
| 4,175,059 | 11/1979 | Edwards et al. ..................... | 252/455 Z |
| 4,176,090 | 11/1979 | Vaughan et al. ..................... | 252/455 Z |
| 4,381,255 | 4/1983 | Nozemack et al. ................. | 252/455 Z |
| 4,381,256 | 4/1983 | Hildebrandt .............................. | 502/68 |
| 4,424,144 | 1/1984 | Pryor et al. ................................ | 502/68 |
| 4,522,705 | 6/1985 | Chu et al. ................................ | 208/120 |
| 4,582,815 | 4/1986 | Bowes ....................................... | 502/64 |
| 4,626,609 | 12/1986 | Shihabi ................................... | 585/467 |
| 4,677,239 | 6/1987 | Dewing et al. ......................... | 585/475 |
| 4,847,224 | 7/1989 | Fajula et al. ............................. | 502/67 |
| 4,861,571 | 8/1989 | Harada et al. .......................... | 423/709 |
| 4,977,120 | 12/1990 | Sakurada et al. ........................ | 502/64 |
| 5,011,667 | 4/1991 | Kuznicki et al. ....................... | 423/118 |
| 5,026,531 | 6/1991 | Tannous et al. ........................ | 423/328 |
| 5,132,260 | 7/1992 | Plee .......................................... | 502/64 |
| 5,145,659 | 9/1992 | McWilliams ............................ | 423/328 |
| 5,460,796 | 10/1995 | Verduyn ................................. | 423/700 |

FOREIGN PATENT DOCUMENTS

| | | |
|---|---|---|
| 11059/35A | 8/1995 | China . |
| 0110650 | 6/1984 | European Pat. Off. . |
| 92/12928 | 8/1992 | WIPO . |

*Primary Examiner*—Helane Myers
*Attorney, Agent, or Firm*—Edward F. Sherer

[57] ABSTRACT

There is provided a process for converting hydrocarbons which utilizes a zeolite bound zeolite catalyst that has enhanced performance when utilized in hydrocarbon conversion processes, e.g., catalytic cracking, alkylation, disproportionation of toluene, isomerization, and transalkylation reactions. The catalyst comprises a first zeolite having particles of greater than about 0.1 micron average particle size and a binder comprising second zeolite particles having an average particle size less than said first particles.

28 Claims, 2 Drawing Sheets

HYDROCARBON CONVERSION PROCESS USING A ZEOLITE BOUND ZEOLITE CATALYST

This application is a divisional of application Ser. No. 08/561,674, filed Nov. 22, 1995, now U.S. Pat. No. 5,993,642, which is a continuation-in-part of Ser. No. 08/344,034, filed Nov. 23, 1994 abandoned.

BACKGROUND OF THE INVENTION

This invention relates to zeolite bound zeolites which have enhanced activity, selectivity, and/or activity maintenance when utilized in hydrocarbon conversion processes.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_4$ and $SiO_4$ tetrahedra linked by shared oxygen atoms. The negativity of the tetrahedra is balanced by the inclusion of cations such as alkali or alkaline earth metal ions. In the manufacture some zeolites, non-metallic cations, such as tetramethylammonium (TMA) or tetrapropylammonium (TPA), are present in the synthesis. The interstitial spaces or channels formed by the crystalline network enable zeolites to be used as molecular sieves in separation processes and catalysts for chemical reactions and catalysts carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon and, optionally, aluminum atoms in the crystalline lattice structure thereof, but also materials which contain suitable replacement atoms for such silicon and aluminum.

Synthetic zeolites are usually prepared by crystallization from a supersaturated synthesis mixture. The resulting crystalline product is then dried and calcined to produce a zeolite powder. Although the zeolite powder has good adsorptive properties, its practical applications are severely limited because the powder has no significant mechanical strength.

Mechanical strength may be conferred on a zeolite by forming a zeolite aggregate such as a pill, sphere, or extrudate. An extrudate can be formed by extruding the zeolite in the presence of a non-zeolitic binder and drying and calcining the resulting extrudate. Examples of such binders include materials such as alumina, silica, titanium, and various types of clays.

Although such bound zeolite aggregates have much better mechanical strength than the zeolite powder, when the bound zeolite is used in a catalytic conversion process, the activity, selectivity, activity maintenance, or combinations thereof of the catalyst can be reduced because of the binder. For instance, since the binder is typically present in an amount of up to about 60 wt % of zeolite, the binder dilutes the adsorptive properties of the zeolite. In addition, since the bound zeolite is prepared by extruding the zeolite with the binder and subsequently drying and calcining the extrudate, the amorphous binder can penetrate the pores of the zeolite, otherwise block access to the pores of the zeolite, or slow the rate of mass transfer to the pores of the zeolite which can reduce the effectiveness of the zeolite when used in hydrocarbon conversion processes and other applications. Still further, when a bound zeolite is used in catalytic processes, the binder may affect the chemical reactions that are taking place within the zeolite and also may catalyze undesirable reactions which can result in the formation of undesirable products.

Thus, there is a need for a hydrocarbon conversion process which utilizes a zeolite catalyst which overcomes, or at least mitigates the above described problems.

SUMMARY OF THE INVENTION

It has been suprisingly discovered that a zeolite catalyst which comprises first zeolite particles and utilizes second zeolite particles as a binder results in a catalyst which provides a means of controlling reactions associated with the binder and has improved mass transfer of reactants to the catalyst, and greater access of the reactants to the pores of the zeolite. The acidity of the second zeolite particles is preferably carefully controlled e.g., the acidity of the second zeolite can be the same as the first zeolite particles or the acidity of the second zeolite particles can be higher or lower than the first zeolite particles, so that the performance of the catalyst is further enhanced. The zeolite catalysts of the present invention have enhanced performance when utilized in hydrocarbon conversion processes. The zeolite catalyst of the present invention finds particular application in hydrocarbon conversion processes where catalyst acidity in combination with zeolite structure are important for reaction selectivity. Examples of such processes include catalytic cracking, alkylation, dealkylation, dehydrogenation, disproportionation, and transalkylation reactions. The catalyst of the present invention also finds particular application in other hydrocarbon conversion processes in which carbon containing compounds are changed to different carbon containing compounds. Examples of such processes include hydrocracking, isomerization, dewaxing, oligomerization, and reforming processes.

DETAILED DESCRIPTION OF THE INVENTION

Figure 1:
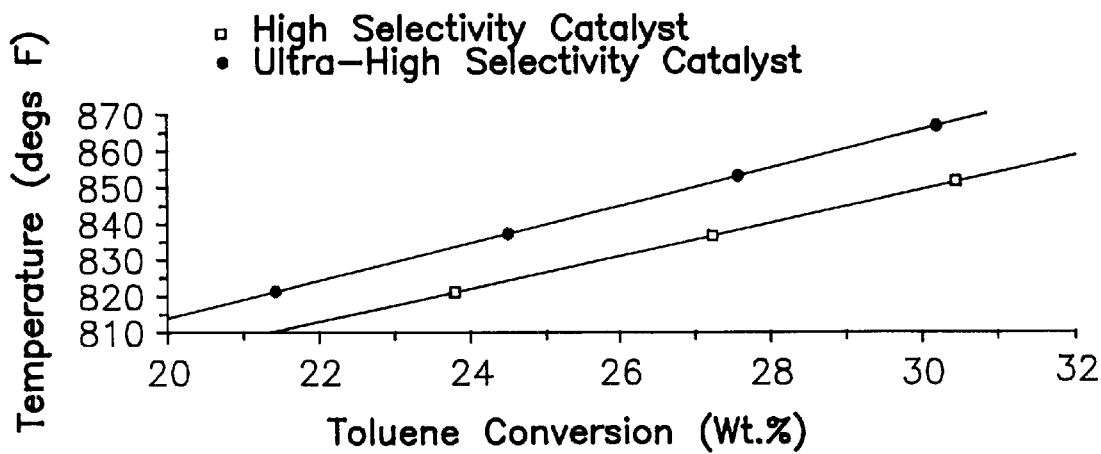
FIGS. 1–4 are graphs demonstrating the activity, paraxylene selectivity, paraxylene yield and benzene yield respectively for the zeolite bound zeolite catalysts of this invention.
Figure 2:
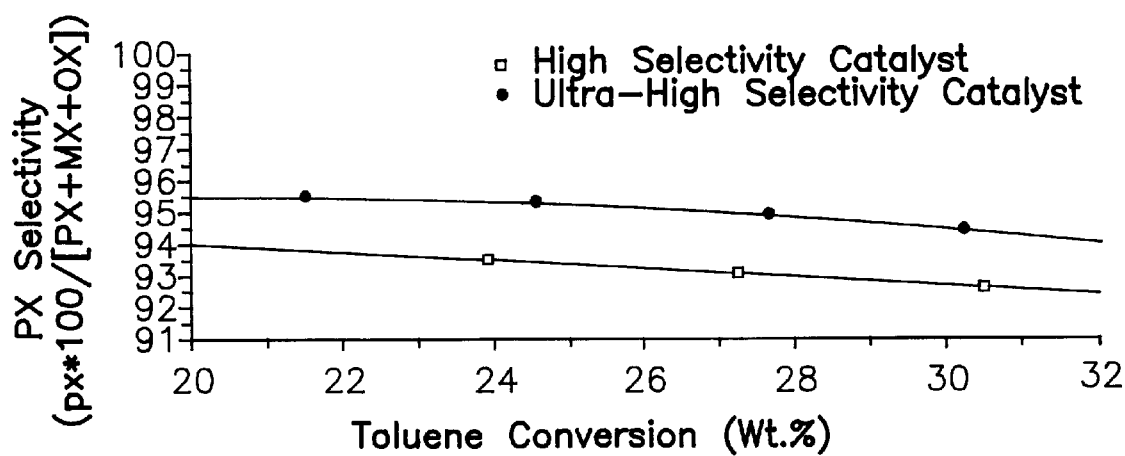
Figure 3:
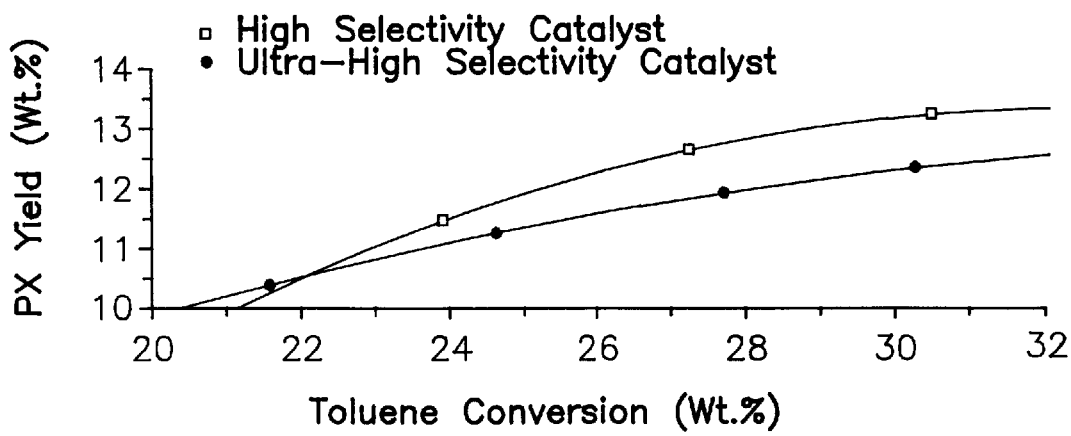
Figure 4:
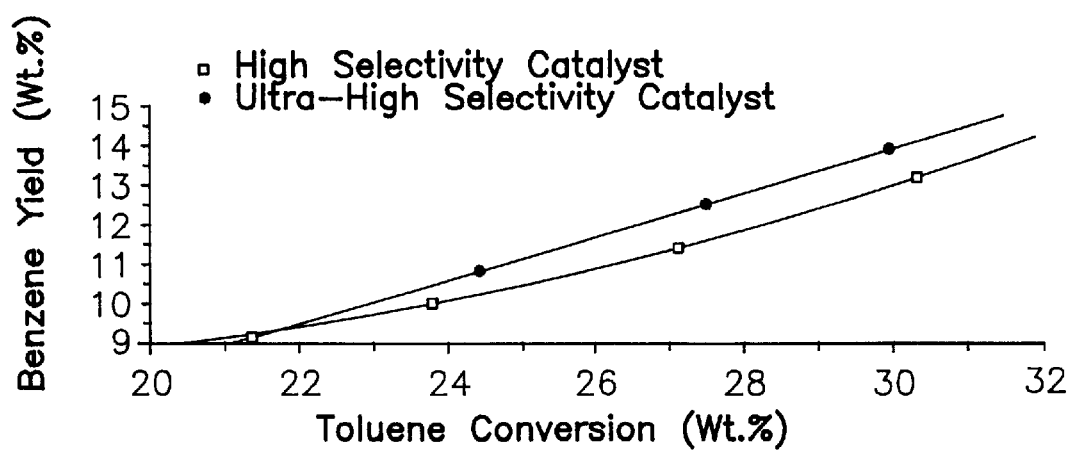

The present invention is directed to a process for converting organic compounds by contacting the organic compounds under conversion conditions with a zeolite bound zeolite catalyst. The zeolite bound zeolite catalyst comprises first zeolite particles which preferably have an average particle size greater than about 0.1 micron average particle size and a binder comprising second zeolite particles having an average particle size of less than said first particles. Typical zeolite particles used as catalysts in hydrocarbon conversion processes are normally bound with silica or alumina or other commonly used amorphous binders to enhance the mechanical strength of the zeolite. The zeolite bound zeolite catalysts of the present invention preferably do not contain significant amounts of non zeolitic binders. Instead, the first zeolite particles of the present invention are bound by the second zeolite particles. The second zeolite particles have an average particle size that is smaller than the first zeolite particles. Preferably, the second zeolite particles bind the first zeolite particles by adhering to the surface of the first particles thereby forming a matrix or bridge structure which also holds the first crystals particles together. More preferably, the second zeolite particles bind the first zeolite particles by intergrowing so as to form a coating or partial coating on the larger first zeolite crystals.

Although the invention is not intended to be limited to any theory of operation, it is believed that the advantages of the zeolite bound zeolite catalyst are obtained by the second zeolite controlling the accessibility of the acid sites on the external surfaces of the first zeolite to reactants. Acid sites existing on the external surface of a zeolite catalyst are believed to affect reactants entering the pores of the zeolite and products exiting the pores of the zeolite. In line with this theory, since the acidity of the second zeolite is carefully selected, the second zeolite does not significantly adversely affect the reactants exiting the pores of the first zeolite which can occur with conventionally bound zeolite catalysts and may beneficially affect the reactants exiting the pores of the first zeolite. Still further, since the second zeolite is not amorphous but, instead, is a molecular sieve, hydrocarbons have increased access to the pores of the first zeolite during hydrocarbon conversion processes. Regardless of the theories proposed, the catalyst, when used in catalytic processes, has the improved properties which are disclosed herein.

The term "average particle size" as used herein, means the average diameter of the particles, e.g., number average of the major axis and minor axis.

The terms "acidity", "lower acidity" and "higher acidity" as applied to zeolite are known to persons skilled in the art. The acidic properties of zeolite are well known. However, with respect to the present invention, a distinction must be made between acid strength and acid site density. Acid sites of a zeolite can be a Bronsted acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species (iii) the local structure of the zeolite, e.g., the pore size and the location, within the crystal or at/near the surface of the zeolite, (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia adsorption.

Examples of zeolites suitable for use in the present invention include large pore zeolites, medium pore zeolites, and small pore zeolites. A large pore zeolite generally has a pore size of >7 Å and includes zeolite types such as MAZ, MEI, FAU, EMT. Examples of large pore zeolites include zeolite L, zeolite Y, zeolite X, offretite, omega, Beta, mordenite, ZSM-3, ZSM-4, ZSM-18, and ZSM-20. A medium pore size catalyst generally has a pore size <7 Å, preferably from about 5 Å to about 6.8 Å; and generally the pore apertures consist of about 10 to 12, preferably about 10, membered ring structures and include MFI, MEL, MTW, EUO, MTT, HEU, FER, and TON. Examples of medium pore zeolite include ZSM-34, ZSM-38, and ZSM-48. A small pore size zeolite has a pore size from about 3 Å to about 5.0 Å. Generally, the pore apertures of the structure consist of from about 8 to 10, preferably about 8, membered ring structures and include CHA, ERI, KFI, LEV, and LTA. Examples of small pore zeolite include ZK-4, ZK-5, zeolite A, zeolite T, gmelinite, chinoptilolite, chabasite and erionite. The zeolites can also comprise gallosilicates and titanosilicates.

The silica to alumina ratio of the first zeolite will generally depend upon the particular hydrocarbon process in which the catalyst is utilized. Generally, however, the first zeolite will have a silica to alumina ratio of at least 2:1, preferably a silica to alumina ratio in the range of from about 10:1 to about 1,000:1, more preferably from about 20:1 to about 500:1. When the catalyst is utilized in the disproportionation of toluene or the cracking of hydrocarbons, the silica to alumina ratio is preferably 30:1 to about 125:1. The average particle size of the first zeolite is preferably from about 0.1 to about 15 microns. In many applications, the average particle size is preferably from about 2 to about 6 microns, and more preferably from about 2 to about 4 microns. In other applications such as the cracking of hydrocarbons, the preferred average particle size is from about 0.1 to about 3.0 microns.

The second zeolite particles are of smaller size than the first zeolite particles. The second zeolite particles generally have an average particle size of less than 1 micron, preferably from about 0.1 to less than 0.5 micron. The silica to alumina ratio of the second zeolite will generally depend upon the particular hydrocarbon process in which the catalyst is utilized. Generally the silica to alumina ratio will be at least 2:1. In applications where low acidity is desired, the second zeolite preferably has a silica to alumina ratio greater than the silica to alumina ratio of the first zeolite, and more preferably is greater than 200:1, e.g., 300:1, 500:1, 1,000:1, etc. In certain applications, the second zeolite is silicalite, i.e., the second zeolite is MFI substantially free of alumina. The pore size of the second zeolite will preferably be a pore size that does not significantly restrict access of the hydrocarbon feedstream to the pores of the first zeolite. For instance, when the materials of the feedstream which are to be converted have a size from 5 Å to 6.8 Å, the second zeolite will preferably be a large pore zeolite or a medium pore zeolite. The second zeolite is preferably present in an amount in the range of from about 10 to about 60% by weight based on the weight of the first zeolite.

The zeolite bound zeolites catalysts of the present invention preferably have an Adsorption Index (AI) greater than 1.00 and more preferably greater than 1.10, and most preferably greater than 1.20 e.g., 1.25, 1.30, etc. The term "Adsorption Index", is defined as the ratio of the weight percent of hydrocarbon (toluene when the first zeolite of the zeolite bound zeolite comprises large pore zeolite or medium pore zeolite and n-hexane when the first zeolite of the zeolite bound zeolite comprises small pore zeolite) adsorbed per amount by weight of zeolite in the zeolite bound zeolite catalyst of the present invention to the weight percent of hydrocarbon (toluene for large pore zeolite and medium pore zeolite and n-hexane for small pore zeolite) adsorbed per amount (by weight) of the first zeolite in the silica bound zeolite catalyst prior to conversion of the silica (after drying and calcination) to the second zeolite of the zeolite bound zeolite catalyst. If the zeolite bound zeolite is not prepared by converting an amorphous silica to a second zeolite, the "Adsorption Index", is defined as the ratio of the weight percent of hydrocarbon (toluene when the first zeolite of the zeolite bound zeolite comprises large pore zeolite or medium pore zeolite and n-hexane when the first zeolite of the zeolite bound zeolite comprises small pore zeolite)

adsorbed per amount by weight of zeolite in the zeolite bound zeolite catalyst of the present invention to the weight percent of hydrocarbon (toluene for large pore zeolite and medium pore zeolite and n-hexane for small pore zeolite) adsorbed per amount (by weight) of the first zeolite of the zeolite bound zeolite catalyst when the first zeolite is bound by 30% by weight of amorphous silica using the method disclosed in Step B. of Example 1. In the determination of the Adsorption Index, all variables used in the procedure to determine the hydrocarbon adsorption of the catalyst remain constant and only the catalyst differs. The Adsorption Index finds particular application when the second zeolite is a medium pore or large pore zeolite.

Procedures which can be utilized to determine the adsorption of toluene for large pore zeolite and medium pore zeolite and n-hexane for small pore zeolite to measure the Adsorption Index of a zeolite catalyst are known to persons skilled in the art. A preferred procedure, hereinafter referred to as the "ZHA Procedure", involves the use of a thermogravimetric analyzer for measuring the weight of adsorbed hydrocarbon (i.e., n-hexane or toluene) and comprises first pre-treating a zeolite catalyst, in this example a small pore zeolite, in a 210 mL/min air flow with the following temperature conditions: holding the catalyst at 30 degrees C. for one minute, next increasing the temperature at 20 degrees C./min to 150 degrees C.; holding the catalyst for 10 minutes at 150 degrees C., then increasing the temperature at 20 degrees C./min to 450 degrees C.; holding the catalyst at 450 degrees C. for 45 minutes, and then cooling the catalyst to 30 degrees C. The weight of the cooled catalyst is then measured and this weight is hereinafter referred to as "W1". Next, a gas containing n-hexane (in this example) in nitrogen is introduced into the chamber containing the catalyst at a temperature 30 degrees C. (P/Po of 0.26) continuously for 60 minutes. For this procedure, P is the partial pressure of adsorbant hydrocarbon and Po is total pressure. The gas is then switched to nitrogen and the sample is desorbed for 60 minutes at 30 degrees C. The weight of the catalyst is then measured and this weight is hereinafter referred to as "W2". The weight percent of hydrocarbon (hexane in this example) adsorbed=[(W2−W1)/W1]×100. When toluene is used for catalysts containing a large pore or medium pore zeolite, the process is the same except that the P/Po of the toluene is preferably 0.15. However, other values of P/Po can be used if precautions are taken to prevent condensation in the transfer lines to the sample chamber. The Adsorption Index can be calculated using the following formula:

$$AI = W(ZBZ)/W(SBZ)$$

wherein W(ZBZ) is weight percent of hydrocarbon (toluene for large and medium pore zeolites or n-hexane for small pore zeolites) adsorbed per amount (by weight) of zeolite bound zeolite (total zeolite weight [excluding any unconverted amorphous silica [excluding any unconverted amorphous silica or other non-zeolite material]); and W(SBZ) is weight percent of hydrocarbon (toluene for large and medium pore zeolites or n-hexane for small pore zeolites) adsorbed per amount (by weight) of zeolite which zeolite is bound with x fraction by weight of amorphous silica. This weight is calculated by measuring total percent hydrocarbon adsorbed (by zeolite+amorphous silica) and dividing that number by (1−x). W(SBZ) is measured on the same silica bound first zeolite aggregate which is converted to the zeolite bound zeolite which is used to measure W(ZBZ) or, if the zeolite bound zeolite is not prepared by converting an amorphous silica to a second zeolite, is measured on a bound zeolite which zeolite is the same as the first zeolite of the zeolite bound zeolite and is bound with 30% by weight of amorphous silica using the method disclosed in Step B. of Example 1.

The Adsorption Index was calculated for the catalysts set forth below. With respect to a silica bound ZK5 zeolite containing 70 wt. % ZK5 and a ZK5 bound with ZK5, the procedure to determine the Adsorption Index was carried out under standard conditions of n-hexane uptake (p/po=0.25, T=30° C.). The silica bound zeolite had a 6.63 wt. % of n-hexane uptake, while the zeolite bound zeolite (100% zeolite) had a n-hexane uptake of 11.10%. These results were converted to the same amount of zeolite. The silica bound ZK5 had a hexane adsorption of 9.45 wt. % (6.63/0.70). The Adsorption Index was determined to be 1.17 (11.10/9.45). A zeolite KL bound zeolite KL and a silica bound zeolite KL containing at least 30% by weight silica were tested using the procedure described above except that toluene was used as the adsorbent. The toluene adsorption was 5.4 wt. % for the silica bound zeolite KL and 10.0 wt. % for the zeolite KL bound zeolite KL. The Adsorption Index was determined to be 1.29.

The catalyst used in the conversion process of the invention can be prepared using various processes but is preferably prepared by a three step procedure. The first step involves the synthesis of a zeolite. Processes for preparing zeolites are known in the art. For example, with respect to the preparation of a MFI zeolite, a preferred process comprises preparing a solution containing tetrapropyl ammonium hydroxide or bromide, alkali metal oxide, an oxide of aluminum, an oxide of silicon and water, heating the reaction mixture to a temperature of 80° C. to 200° C. for a period of from about four hours to eight days. The resulting gel forms solid crystal particles which are separated from the reaction medium, washed with water and dried. The resulting product may then be optionally calcined in air at temperatures of 400–550° C. for a period of 10–40 hours to remove tetrapropylammonium (TPA) cations.

When an MFI is preferred, the MFI can be identified in terms of mole ratios of oxides as follows:

$$0.9 \pm 0.2\ M_{2/n}O:Al_2O_3:5-500\ SiO_2:ZH_2O$$

wherein M is selected from the group consisting of a mixture of alkali metal cations, preferably sodium, and organic ions such as tetralkylammonium cations, the alkyl groups preferably containing 2–5 carbon atoms, and z ranges from 0 to 40. In a more preferred form, the MFI zeolite contains a silica to alumina mole ratio of from about 10:1 to about 300:1.

Next, a silica-bound zeolite is prepared preferably by mulling a mixture comprising the zeolite crystals, a silica gel or sol, water and optionally an extrusion aid until a homogeneous composition in the form of an extrudable paste develops. The silica binder used in preparing the silica bound zeolite aggregate is preferably a silica sol and preferably contains only very minor amounts of alumina, e.g., less than 2,000 ppm, and more preferably less than 1,000 ppm of alumina. The amount of silica formulated at this stage is such that the content of the zeolite in the dried extrudate will range from about 30 to 90% by weight, more preferably from about 55 to 85% by weight, with the balance being primarily silica, e.g. about 15 to 45% by weight silica. The resulting paste is then molded, e.g. extruded, and cut into small strands, e.g., 2 mm diameter extrudates, which are dried at 100–150° C. for a period of 4–12 hours. Preferably the dried extrudates are then calcined in air at a temperature of from about 400° C. to 550° C. for a period of from about 1 to 10 hours. This calcination step also destroys the extrusion aid if present.

Optionally, the silica-bound aggregate can be made into a very small particles which have application in fluid bed processes such as catalytic cracking. This preferably involves mixing the zeolite with a silica containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octaine-Enhancing Zeolitic FCC Catalysts, Julius Scherzer, Marcel Dekker, Inc. New York, 1990). The fluidizable silica-bound aggregate particles, like the silica bound extrudates described above, would then undergo the final step described below to convert the silica binder to a second zeolite.

The final step in the three step catalyst preparation process is the conversion of the silica present in the silica-bound catalyst to a second zeolite which serves to bind the residual the zeolite particles together. The first zeolite crystals are thus held together without the use of a significant amount of non-zeolite binder. The resulting zeolite catalyst preferably contains less than 10% by weight (based on the weight of the first and second zeolite) of non zeolitic binder, more preferably less than 5% by weight, and, most preferably less than 3% by weight of non zeolitic binder.

To prepare the zeolite bound zeolite, the silica-bound aggregate is preferably first aged in an appropriate aqueous solution at elevated temperature. Next, the contents of the solution and the temperature at which the aggregate is aged should be selected to convert the amorphous silica binder into a second zeolite. In certain applications, e.g., disproportionation of toluene, it is preferable that the second zeolite be the same as the initially bound zeolite or a crystallographic match for the initially bound zeolite. The newly-formed zeolite is produced as crystals. The crystals may grow on and/or adhere to the initial zeolite crystals, and may also be produced in the form of new intergrown crystals, which are generally much smaller than the initial crystals, e.g., of sub-micron size. These-newly formed crystals may grow together and interconnect thereby causing the larger crystals to become bound together.

The nature of the zeolite formed in the secondary synthesis conversion of the silica to zeolite may vary as a function of the composition of the secondary synthesis solution and synthesis aging conditions. The secondary synthesis solution is an aqueous ionic solution containing a source of hydroxy ions sufficient to convert the silica to the desired zeolite. For instance, in the manufacture of an MFI-type zeolite, the solution will have an initial molar ratio of OH:ions to $SiO_2$ up to a level of up to about 1.2. An MFI-type zeolite may be formed by aging in a solution containing a source of tetrapropylammonium (TPA) and optionally a source of alumina and optionally a source of Na+; a MEL-type zeolite may be formed by aging in a solution containing a source of tetrabutyl ammonium and a source of Na+. Suitable aqueous solutions for these and other medium pore zeolites are known to persons skilled in the art. It is important, however, that the aging solution be of a composition which will not cause the silica present in the bound zeolite extrudate to dissolve out of the extrudate. Also, in some instances, it is preferable that the zeolite formed in the secondary synthesis is less acidic than the core zeolite.

In a preferred embodiment of the invention, the aqueous ionic solution in which the bound zeolite is aged contains a source of hydroxy ions (preferably NaOH). When manufacturing an MFI-type zeolite, the initial molar ratio of $OH^-$ to $SiO_2$ is preferably at a level of up to about 1.2, more preferably from about 0.05 to 1.2, and most preferably from about 0.07 to 0.15. This treatment causes the silica binder to be converted substantially to a MFI-type zeolite, but of lower acidity as reflected by having a significantly higher silica to alumina ratio. The solution also contains a template (e.g., source of tetraalkyl ammonium ions for MFI-type zeolite) and may optionally include a source of alumina and a source of $Na^+$ ions. The silica to alumina ratio of the converted binder is thus controlled by controlling the composition of the aqueous solution. If the silica binder material which is converted and the secondary synthesis mixture are substantially free of alumina, the converted material is more appropriately called silicalite. It important that the aging solution have a pH which is not too alkaline. This may be achieved, when producing a MFI-type bound zeolite, by using a solution having an initial molar ratio of $OH^-$:$SiO_2$ of 0.05 to 1.2. Generally ratios of 0.07 to 0.15 are preferred. If the ratio is too high (i.e. the solution has high alkalinity), the bound crystals will dissolve in the solution. The silica binder, instead of being converted into zeolite crystals on the core zeolite crystals, or forming intergrown crystals, dissolves out of the extrudate and crystallizes outside the zeolite core crystals in the surrounding mother liquor. This weakens or destroys the integrity of the extrudate. The more alkaline the aging solution the more the silica dissolves out of the extrudate. Aging of the zeolite extrudate in the aging solution is preferably conducted at elevated temperatures, generally in the range of from about 95 to 200° C., more preferably in the range of about 130 to 170° C., most preferably in the range of about 145 to 155° C. Aging time may range from about 20 to 140 hours, more preferably from about 60 to 140 hours, most preferably from about 70 to 80 hours.

After aging, the zeolite is separated from solution, washed, dried and calcined.

A preferred process for preparing a binderless MFI-type zeolite comprises mixing a solution containing sodium ions e.g. aqueous sodium hydroxide, with a solution containing TPA ions, e.g., a TPA halide solution, such as TPA bromide. The silica-bound extrudate of the second step may then be added and the composition heated to preferably 140 to 160° C., most preferably about 150° C. The material is maintained at this temperature for 60 to 140 hours, preferably 70 to 80 hours. The resulting product may then be washed and dried. To remove the $TPA^+$ species, the product is calcined after washing, preferably at a temperature of 450 to 550° C.

In certain applications, e.g., disproportionation of toluene, the most preferred MFI bound catalyst may be described as a two phase catalyst comprising a first phase of particles of MFI-type zeolite having a silica to alumina ratio of from about 10:1 to about 200:1. The second phase is comprised of MFI-type zeolite having a higher silica to alumina ratio in excess of about 200:1. The second phase consists of small intergrown crystals that cover or partially cover the first phase particles and of small crystalline particles that adhere to the surface of the first phase particles. Preferably the first phase particles have a silica to alumina ratio of from about 20:1 to 150:1, more preferably from about 50:1 to 125:1, and the second phase has a silica to alumina ratio greater than about 200:1, more preferably greater than about 300:1. The particle size of the first phase particles may be in the range of conventional MFI-type zeolite particle size, i.e., an average particle size of from about 0.1 to 15 microns, more preferably from about 1–5 microns, and most preferably about 2 to 4 microns. The second phase particles which serve to adhere the first phase particles together are of much smaller size, generally having an average particle size of less than one micron, preferably of from about 0.1 to less than 0.5 micron.

The zeolites of the present invention may be further ion exchanged as is known in the art either to replace at least in part the original alkali metal present in the zeolite with a different cation, e.g. a Group 1B to VIII Periodic Table metal such as nickel, copper, zinc, palladium, platinum, calcium or rare earth metal, or to provide a more acidic form of the zeolite by exchange of alkali metal with intermediate ammonium, followed by calcination of the ammonium form to provide the acidic hydrogen form. The acidic form may be readily prepared by ion exchange using a suitable acidic reagent such as ammonium nitrate. The zeolite may then be calcined at a temperature of 400–550° C. for a period of 10–45 hours to remove ammonium cations. Ion exchange is preferably conducted after formation of the two phase zeolite bound zeolite catalyst. Particularly preferred cations are those which render the material catalytically active, especially for certain hydrocarbon conversion reactions. These include hydrogen, rare earth metals, and metals of Groups IIA, IIIA, IVA, IB, IIB, IIIB, IVB, and VIII of the Periodic Table of the Elements.

The zeolite-bound catalysts as described above have mechanical strength which is at least comparable to and often stronger than that of silica-bound zeolite aggregate. For example typical crush strengths of the silica-bound and zeolite-bound materials compare as follows:

| | CRUSH STRENGTH |
|---|---|
| SiO$_2$ bound extrudate | 0.46 kgf/cm$^2$ |
| MFI-type-bound | 1.28 kgf/cm$^2$ |

The zeolite-bound catalyst also has absorption properties comparable with that of the zeolite powder.

The most preferred zeolite-bound MFI catalysts for use in reactions such as toluene disproportionation comprise discrete, rounded core MFI-type crystal particles having crystal size of from about 2–4 microns and a silica/alumina ratio of 60:1 to 100:1 and binder particles of smaller crystal size, generally from about 0.1 to less than 0.5 microns, having a silica/alumina ratio of about 200:1 or greater, e.g., from 750:1 to 5,000:1.

Processes for preparing the catalysts useful in the present invention are disclosed in the copending U.S. application Ser. No. 08/335,222, filed Nov. 7, 1994, now U.S. Pat. No. 5,460,769, and Ser. No. 08/344,034, filed Nov. 11, 1994, the disclosures of which are hereby incorporated by reference.

The zeolite bound zeolites of the present invention can be used in processing hydrocarbonaceous feedstocks. Hydrocarbonaceous feed-stocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbonaceous feed is to undergo, the feed can contain metal or can be free of metals. Also, the feed it can also have high or low nitrogen or sulfur impurities.

The conversion of hydrocarbonaceous feeds can take place in any convenient mode, for example, in fluidized bed, moving bed, or fixed bed reactors depending on the types of process desired.

Since the zeolite bound zeolite catalysts of the present invention have controlled acidity and do not contain a conventional binder which can adversely affect the access and/or contact of reactants to and with the active sites of the catalyst and can also cause undesirable side reactions to occur, the zeolite bound zeolite of the present invention by itself or in combination with one or more catalytically active substances can have high activity, high selectivity, high activity maintenance, or combinations thereof when used as catalysts for a variety of organic, e.g., hydrocarbon compound conversion processes. Examples of such processes include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst÷feed rate from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 1000 and an aromatic hydrocarbon/polyalkylaromatic hydrocarbon mole ratio of from about 1/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 hr$^{-1}$ to about 2,000 hr$^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 hr$^{-1}$ to about 2000 hr$^{-1}$ and an aromatic hydrocarbon/olefin mole ratio of from about 1/1 to about 20/1. The resulting product from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 hr$^{-1}$ to about 50 hr$^{-1}$;

(I) The hydrocracking of heavy petroleum feedstocks, cyclic stocks, and other hydrocrack charge stocks. The zeolite bound zeolite catalyst will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Typical reaction conditions include temperatures from about 100° C. to about 250° C., a pressure of from about 100 to about 800 psig, a WHSV -olefin from about 0.4 hr$^{-1}$ to about 0.8 hr$^{-1}$, a WHSV -reformate of from about 1 hr$^{-1}$ to about 2 hr$^{-1}$ and, optionally, a gas recycle from about 1.5 to 2.5 vol/vol fuel gas feed.

(K) ( The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 160° C. to about 260° C. and pressures from about 350 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 hr$^{-1}$ to about 10 hr$^{-1}$.

(M) The conversion of light paraffins to olefins and/or aromatics. Typical reaction conditions include temperatures from about 425° C. to about 760° C. and pressures from about 10 to about 2000 psig.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals processing steps in a first stage using in the first stage the zeolite bound zeolite catalyst comprising one or more catalytically active substances, e.g., a Group VIII metal, and the effluent from the first stage would be reacted in a second stage using a second zeolite, e.g., zeolite Beta, comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the zeolite bound zeolite catalyst comprising a hydrogenation component and zeolite Beta. Typical reaction conditions including temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions including temperatures from about 20° C. to about 200° C., pressures from 2 to about 200 atm, WHSV (gram-olefin per hour gram-zeolite) from about 0.1 hr$^{-1}$ to about 200 hr$^{-1}$ and an alcohol to olefin molar feed ratio from about 0.1/1 to about 5/1.

(R) The disproportionation of toluene to make benzene and paraxylene. Typical reaction conditions including a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g. C6–C10) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) The adsorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a zeolite bound zeolite at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite bound zeolite catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, therefore, catalytic conversion conditions over a catalyst comprising the zeolite bound zeolite include a temperature of from about 100° C. to about 760° C., a pressure of from about 0.1 atmosphere (bar) to about 200 atmospheres (bar), a weight hourly space velocity of from about 0.08 hr$^{-1}$ to about 2,000 hr$^{-1}$.

Although many hydrocarbon conversion processes prefer that the second zeolite crystals have lower acidity to reduce undesirable reactions external to the first zeolite crystals, some processes prefer that the second zeolite crystals have higher acidity, e.g., the acidity be tailored so as to catalyze desirable reactions. Such processes are of two types. In the first type, the acidity and the crystallographic type of the second zeolite is tailored to match the acidity and the crystallographic type of the first zeolite. By doing so, the catalytically active material per weight of formed catalyst will be increased thereby resulting in increased apparent catalyst activity. Such a catalyst would also be benefited by the greater adsorption, e.g., accessibility and reduced non-selective surface acidity. Toluene disproportionation is an example of a process that would be benefited by this type of catalyst. With toluene disproportionation, a non-selective, equilibrium mixture of xylenes in the product is desired and, therefore, greater formed catalyst apparent activity is more beneficial than improved selectivity.

The second type of process that can be benefited by tailoring the acidity of the second zeolite phase is one where two or more reactions are taking place within the zeolite catalyst. In such a process, the acidity and/or the crystallographic structure of the second phase zeolite may be tailored so that it is different than that of the first zeolite, but does not have to be essentially void of acidic sites. Such a catalyst would be comprised of two different zeolites that could each be separately tailored to promote or inhibit different reactions. A process using such a catalyst would not only benefit from greater apparent catalyst activity, greater zeolite accessibility, and reduced non-selective surface acidity possible with zeolite bound zeolites, it would also benefit from a tailored product.

Combined xylene isomerization/ethylbenzene dealkylation processes would benefit from this type of catalyst. An isomerization/ethylbenzene dealkylation catalyst could be tailored such that ethylbenzene dealkylation would primarily occur within the first zeolite crystals, and xylenes isomerization would primarily occur within the second zeolite crystals. By tailoring a catalyst in this way, a balance between the two reactions can be achieved that could not otherwise be achieved with a catalyst containing only one zeolite.

The zeolite-bound catalyst of the present invention has particular application in the vapor phase disproportionation of toluene. Such vapor phase disproportionation comprises contacting toluene under disproportionation conditions with the zeolite bound zeolite catalyst to yield a product mixture which comprises a mixture of unreacted (unconverted) toluene, benzene and xylene. In the more preferred embodiment, the catalyst is first selectivated prior to use in the disproportionation process to enhance conversion of toluene to xylene and to maximize the catalyst selectivity towards the production of paraxylene. Processes for selectivating the catalyst are known to persons skilled in the art. For instance, selectivation may be accomplished by exposing the catalyst in a reactor bed to a thermally decomposable organic compound, e.g. toluene, at a temperature in excess of the decomposition temperature of said compound, e.g. from about 480° C. to about 650° C., more preferably 540° C. to 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst. The initial mole ratio of hydrogen gas to toluene present in the toluene feed stream can be reduced during the selectivation process after a significant amount of coke has been deposited on the catalyst surface.

Selectivation of the catalyst can also be accomplished by treating the catalyst with a selectivation agent such as an organosilicon compound. Organosilicon compounds suitable for use as a selectivation agent are disclosed in U.S. Pat. No. 5,365,003, which is hereby incorporated by reference.

When used in the vapor phase disproportionation of toluene, the catalyst more preferably comprises a first phase of particles of MFI-type zeolite crystallites having a micron average particle size from about 3 to about 4, a silica to alumina mole ratio of from about 70 to about 80:1, having adhered structurally to the surfaces thereof particles of a second MFI or MFI-type binder phase having an average particle size of less than about 0.1 micron and having a alumina to silica ratio in excess of about 300:1 to about 10,000:1 and most preferably greater than 900:1.

Selectivated versions of the zeolite bound zeolite when used in vapor phase disproportionation exhibit a higher selectivity towards the production of paraxylene than conventional selectivated MFI catalysts.

The catalyst of the invention is more resistant to coking than conventional catalysts used in disproportionating. For instance, a selectivation process involving the disproportionation of coke for a conventional catalyst normally requires at least 24 hours until sufficient coke has built up to the point where paraxylene production is maximized. Conventional MFI catalysts are less resistant to coking and can therefore be selectivized in less time. However, because a conventional ZSM-5 catalyst is less resistant to coking, it will be more quickly deactivated during its use in disproportionation, giving rise to shorter run cycles. Thus, one of the major advantages of the use of the zeolite bound zeolite in vapor phase disproportionation, is longer disproportionation cycle lengths.

Once the catalyst has been selectivated to the desired degree, e.g., greater than 80% paraxylene selectivity at on-oil conditions, reactor selectivation conditions are changed to disproportionation conditions. These disproportionation conditions include a temperature between about 400° C. and 550° C., more preferably between about 425° C. and 510° C., at a hydrogen to toluene mole ratio of from 0 to about 10, preferably between about 0.1 and 5 and more preferably from about 0.1 to less than 1, at a pressure between about 1 atmosphere and 100 atmospheres and utilizing WHSV of between about 0.5 and 50. One of the particular advantages of the use of the catalyst in disproportionation is that it provides a good paraxylene selectivity at $H_2$/toluene mole ratios of less than 1, e.g. at about 0.5.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

The zeolite bound zeolite of the present invention is also especially useful as a catalyst in a process for isomerizing one or more xylene isomers in a $C_8$ aromatic feed to obtain ortho-, meta-; and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. At the same time, part of the ethylbenzene in the feed is converted to xylenes or to products which are easily separated by distillation. The isomerate is blended with fresh feed and the combined stream is distilled to remove heavy and light by-products. The resultant $C_8$ aromatics stream is then recycled to repeat the cycle.

It is important that xylene isomerization catalysts produce a near equilibrium mixture of xylenes and it is also sometimes desirable that the catalysts convert ethylbenzene with very little net loss of xylenes. The zeolite bound zeolites find particular application in this regard. The silica to alumina ratios of the first zeolite and second zeolite can be selected to balance xylene isomerization and ethylbenzene dealkylation while minimizing undesirable side reactions. Accordingly, an additional aspect of the present invention is to provide a hydrocarbon conversion process which comprises contacting a $C_8$ aromatic stream containing one or more xylene isomers or ethylbenzene or a mixture thereof, under isomerization conditions with the zeolite bound zeolite.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 3.0 to 30.0 moles of hydrogen per mole of alkylbenzene. If hydrogen is used, the catalyst should comprise 0.1 to 2.0 wt % of a hydrogenation/dehydrogenation component selected from Group VIII of the Periodic Table, especially platinum, palladium, or nickel. By Group VIII metal component is meant the metals and their compounds such as oxides and sulfides.

In the liquid phase, suitable isomerization conditions include a temperature in the range 150° C.–375° C., a pressure in the range 1–200 atm abs, and a WHSV in the range 0.5–50. Optionally, the isomerization feed may contain 10 to 90 wt % of a diluent such as toluene, trimethylbenzenes, naphthenes, or paraffins.

The zeolite bound zeolites of the present invention are especially useful as a catalyst in a process for cracking a $C_4^+$ naphtha feed, particularly a $C_4^-$ 290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The zeolite bound zeolites of the present invention are especially useful as a catalyst in the transalkylation of polyalkylaromatic hydrocarbons. Examples of suitable polyalkylearomatic hydrocarbons include di-, tri-, and tetra-alkyl aromatic hydrocarbons, such as diethylbenzene, triethylbenzene, diethylmethylbenzene (diethyltoluene), diisopropylbenzene, triisopropylbenzene, diisopropyltoluene, dibutylbenzene, and the like. Preferred polyalkylaromatic hydrocarbons are the dialkyl benzenes. Particularly preferred polyalkylaromatic hydrocarbons are diisopropylbenzene and diethylbenzene.

The transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C. to maintain at least a partial liquid phase, and the pressure will be preferably in the range of about 50 psig to 1,000 psig, preferably 300 psig to 600 psig. The weight hourly space velocity will range from about 0.1 to 10.

The following example illustrates a process for the preparation of a zeolite bound zeolite catalyst useful in the present invention.

EXAMPLE 1

A. Preparation of MFI-type Zeolite 20.4 kg of a synthesis mixture with a molar composition of:

$$0.45\ Na_2O/0.9\ TPA\ Br/0.125\ Al_2O_3/10\ SiO_2/146H_2O$$

was aged at 150° C. for five days without stirring in a 25 liter stainless steel autoclave. The resulting product was washed with water to pH 10.2 and dried at 120° C. for about 16 hours. A portion of the product was calcined in air at 475° C. for 32 hours. Characteristics of the calcined product:

XRD: Pure MFI.

SEM: –3 micron spherical crystallites.

Elemental: $SiO_2/Al_2O_3$ ratio=80.

B. Preparation Silica-bound Particles

A portion of the calcined product of (A) above was formed into 2 mm diameter extrudates with silica as follows:

| COMPONENTS USED FOR PREPARATION | QUANTITY (grams) |
|---|---|
| MFI crystals (dried at 250° C. for 2 hours) | 200.00 |
| $H_2O$ | 49.75 |
| $SiO_2$ gel (AEROSIL 300) | 18.82 |
| Silica sol (NALCOAG 1034A) | 197.24 |
| Extrusion aid (hydroxypropyl methyl cellulose) | 1.07 |

The above components were mixed in a food processor in the order shown. About 6 minutes after adding the extrusion aid, a thick and smooth paste was obtained. The paste was extruded into 2 mm diameter extrudates. The extrudates were dried overnight at 130° C. and then calcined at 510° C. for 6 hours in air.

Composition of calcined silica-bound extrudates:

MFI: 69.96 wt %

$SiO_2$ binder: 30.04 wt %

C. Conversion to Zeolite bound Zeolite

Preparation synthesis mixture:

| COMPONENTS USED FOR PREPARATION | QUANTITY (grams) |
|---|---|
| Solution A: | |
| NaOH pellets (98.3%) | 1.16 |
| $H_2O$ | 24.63 |
| Additional rinse water | 10.02 |
| Solution B: | |
| Tetrapropylammoniumbromide | 8.00 |
| $H_2O$ | 25.47 |
| Additional rinse water | 18.89 |

Solution A was poured together with the additional water into a 300 ml stainless steel autoclave.

Solution B was poured together with the additional water into the contents of the autoclave. The two solutions were mixed. Finally, 60.04 grams of the silica-bound MFI-type extrudates prepared as above (pre-dried for 2 hours at 150° C.) were added to the synthesis mixture in the autoclave.

The composition of the mixture in the autoclave was:

0.48 $Na_2O$/1.00 TPA Br/10 $SiO_2$/147 $H_2O$ ($OH^-$:$SiO_2$ ratio –0.1)

The amount of MFI crystals in this mixture was 40.5 wt % based on the total weight of the mixture. The autoclave was heated up to 150° C. and kept at this temperature for 71 hours. After this aging period, the autoclave was opened and the product was collected.

The product was washed in a Beuchner funnel with 4250 ml of water in 11 portions and the pH of the last wash water was 10.2. The product was dried for three hours at 150° C. Weight of product recovered after drying: 62.5 grams. The product was significantly harder than the starting silica-bound extrudates. The product was calcined in air for 18 hours at 500° C. to remove the $TPA^+$-species. Weight loss after calcination was 5.8 wt %.

The product was characterized by x-ray diffraction (XRD), scanning electron microscopy (SEM) and hexane adsorption, with the following results:

- XRD: % crystallinity increase vs. starting silica bound extrudates: 32% (height increase of peaks at d values between 3.02 and 2.96 A).
- SEM: 10,000 times micrographs showed that the –3 micron MFI crystallites of preparation (A) were and coated with intergrown, newly formed submicron crystallites. There was no visible trace of the amorphous silica which was plainly visible in the micrographs of the starting-extrudates.
- Silica To Alumina ratio
- MFI crystallites of preparation A—80:1
- Newly formed submicron crystallites—900:1

The following examples illustrate the selectivation and disproportionation processes of the invention.

EXAMPLE 2

The calcined, zeolite-bound catalyst described in Example 1 was selectivated by feeding toluene across the catalyst under the following conditions to produce a high selectivity catalyst:

| Selectivation Conditions | | |
|---|---|---|
| Hours | | 340 |
| Temperature (° F.) | | 1100 |
| Pressure (Psig) | | 225 |
| WHSV (#Feed/#Cat/hr.) | | 1 |
| H2:Feed Toluene Ratio (moles) (Ratio decreased during selectivation to expedite selectivation) | Initial | 0.5:1 $H_2$:Feed Tol. Ratio |
| | Final | 0.35:1 $H_2$:Feed Tol. Ratio |
| Hydrocarbon Partial Pressure | Initial | 60 Psia |
| | Final | 63 Psia |

After about 340 hours at selectivation conditions, selectivation was terminated at the point where about 92–94% selectivity to para-xylene would be achieved at normal disproportionation conditions.

Following selectivation, the high selectivity catalyst was used for the selective disproportionation of toluene (STDP) under the following test conditions:

On-oil Conditions
- Temperature (° F.)—Varied within 805°–860°
- Pressure (Psig)—300
- WHSV—3# feed/lb. cat./hr.
- H2:Feed Toluene Ratio (moles)—2:1
- Hydrocarbon Partial Pressure—93.4 Psia The on-oil catalyst performance for the high selectivity catalyst is shown in FIGS. 1–4.

Upon completion of the test runs described above, the zeolite-bound catalyst used in the tests was once again selectivated under the selectivation conditions described above for an additional 20 hours to produce an ultra-high selective catalyst. Additional STDP tests were then conducted under the STDP conditions described above. These results are also shown in FIGS. 1–4.

By selectivating the catalyst further after running at disproportionation conditions, some of the catalyst's activity was lost as demonstrated in FIG. 1. The temperature required to achieve a targeted conversion was a few degrees greater than with a conventional ZSM-5 catalyst. However, FIG. 2 demonstrates that the para-xylene (PX) selectivity of the zeolite-bound catalyst was increased to 94–95%, an ultra-high selectivity for STDP.

EXAMPLE 3

A conventional ion exchanged, alumina-bound HZSM-5 disproportionation catalyst was selectivated by feeding toluene across the catalyst. The zeolite-bound MFI catalyst of this invention was also selectivated. Selectivation conditions were as follows:

| Catalyst SELECTIVATION CONDITIONS | Conventional ZSM-5 | Zeolite-Bound MFI |
|---|---|---|
| Hours | 55 | 163 |
| Temperature (° F.) | 1075 | 1100 |
| Pressure (Psig) | 225 | 225 |
| WHSV (#/#/hr.) | 2 | 1 |
| H2:Feed Toluene Ratio (moles) | 0.5:1 | 0.25:1 |
| Hydrocarbon Partial Pressure (Psia) | 60 | 64.2 |

Following selectivation, the conventional HZSM-5 catalyst and the zeolite-bound MFI catalyst of this invention were used for the disproportionation of toluene under test conditions shown in Table 1 below. The zeolite bound zeolite catalyst was evaluated under 3 separate test conditions as shown in Table 1. On-oil catalyst performance for each catalyst is also shown in the table.

TABLE 1

On-Oil Conditions

|  | ZSM-5 | ← Zeolite-bound ZSM-5 → | | |
|---|---|---|---|---|
|  |  | Test Case 1 | Test Case 2 | Test Case 3 |
| Temperature (° F.) | 850 | 843 | 827 | 839 |
| Pressure (Psig) | 300 | 300 | 300 | 300 |
| WHSV (#/# hr.) | 3 | 3 | 3 | 4.2 |
| H2:Feed Toluene Ratio (moles) | 2 | 2 | 2 | 0.5 |
| Hydrocarbon Partial Pressure | 93.4 | 93.4 | 93.4 | 196.1 |

On-Oil Catalyst Performance

|  | ZSM-5 | ← Zeolite-bound ZSM-5 → | | |
|---|---|---|---|---|
| Toluene Conversion (wt. %) | 24.1 | 28.4 | 25.0 | 30.1 |
| Paraxylene Selectivity (PX/[PX + MX + OX]× 100) | 82.1 | 94.0 | 94.8 | 93.0 |
| Benzene Yield (wt. %) | 10.2 | 13.0 | 11.1 | 13.6 |
| Xylene Yield (wt. %) | 12.1 | 13.4 | 12.4 | 14.7 |
| $C_5$-Yield (wt. %) | 1.1 | 0.9 | 0.6 | 0.6 |
| $C_9^+$Yield (wt. %) | 0.5 | 0.6 | 0.5 | 0.8 |

Selectivation of the conventional catalyst was completed in less than 55 hours. At this point, the conventional catalyst had a coke content of about 34% by weight. By comparison, the zeolite-bound catalysts of this invention typically contained less than 15% by weight coke.

The fact that zeolite-bound MFI catalyst selectivated much slower than conventional MFI catalyst even though more severe selectivation conditions were used is significant. The long time required for the zeolite bound zeolite catalyst selectivation demonstrates that it is very resistant to coking. Since coking is the major cause for catalyst deactivation, the zeolite-bound catalyst deactivates more slowly than conventional ZSM-5 and therefore offers longer cycle lengths. The reason for the zeolite-bound catalyst's resistance to coking is that it has lower MFI nonchannel surface acidity and therefore lower activity for the formation of coke precursors. Lower deactivation rate due to greater resistance to coking is one of the advantages of this invention.

The standard ZSM-5 catalyst was not selectivated as long nor to the degree of the zeolite-bound catalyst because considerable activity loss was apparent during selectivation even though the standard catalyst's selectivation conditions were considerably less severe than those of the zeolite-bound catalyst. The catalyst could have been selectivated to a greater selectivity but at a considerable sacrifice of catalyst activity. The selectivation was terminated at a point which best balanced catalyst activity and selectivity.

The results clearly show that the zeolite-bound catalyst is more active and selective following selectivation. Furthermore, the greater time of selectivation even though greater severity selectivation conditions were used, demonstrates the zeolite-bound catalyst's resistance to coking.

To further demonstrate zeolite-bound catalyst's resistance to coking, the catalyst was subjected to on-oil operations at the severe conditions of 4 WHSV, 835° F., 300 psig, and 0.5 $H_2$:oil ratio for a period of 17 days. Initial catalyst lined-out performance at these conditions was:
Conversion: 31.0%
PX Selectivity: 94.7%
BZ Yield: 14.0%
PX Yield: 13.9%
After 17 days, the catalyst performance was:
Conversion: 31.0%
PX Selectivity: 95.1%
BZ Yield: 14.2%
PX Yield: 14.1%

This test demonstrates no activity loss (actually a slight gain) during 17 days. Thus, the catalyst is very resistant to coking.

The zeolite-bound MFI catalyst has increased catalyst activity, greater PX selectivity, improved PX yield, and greater resistance to deactivation by coking than does conventional MFI catalyst.

EXAMPLE 4

The zeolite-bound ZSM-5 catalyst of this invention was selectivated and evaluated under the four different test conditions shown in Table 2.

TABLE 2

| Selectivation Conditions | | |
|---|---|---|
| Hours |  | 168 |
| Temperature (° F.) |  | 1100 |
| Pressure (Psig) |  | 225 |
| WHSV (#feed/#cat./hr.) |  | 1 |
| $H_2$:Feed Toluene Ratio (Ratio decreased | Initial | 0.25:1 |
| during selectivation to expedite selectivation) | Final | 0.15:1 |
| Hydrocarbon Partial Pressure | Initial | 64.2 |
|  | Final | 66.0 |

| On-Oil Conditions | Test Case 1 | Test Case 2 | Test Case 3 | Test Case 4 |
|---|---|---|---|---|
| Temperature (° F.) | 835 | 813 | 835 | 818 |
| Pressure (Psig) | 300 | 300 | 300 | 300 |
| WHSV (#/#/hr) | 4.2 | 3 | 3 | 3 |
| H2:Feed Toluene Ratio (moles) | 0.5:1 | 0.5:1 | 2:1 | 2:1 |
| Hydrocarbon Partial Pressure (Psia) | 196.1 | 196.1 | 93.4 | 93.4 |

| On-Oil Catalyst Performance | Test Case 1 | Test Case 2 | Test Case 3 | Test Case 4 |
|---|---|---|---|---|
| Feed(100% Toluene) Conversion(wt. %) | 31.0 | 30.2 | 28.2 | 25.0 |
| Paraxylene Selectivity (PX/[PX+MX+OX]X100) | 94.6 | 94.0 | 95.6 | 95.9 |
| Benzene Yield (wt. %) | 14.0 | 13.4 | 12.7 | 10.9 |
| Xylene Yield (wt. %) | 14.7 | 14.8 | 12.8 | 11.9 |
| $C_{5-}$ Yield (wt. %) | 0.9 | 0.8 | 1.7 | 1.3 |
| $C_9^+$ Yield (wt. %) | 0.9 | 0.8 | 0.6 | 0.5 |

In Example 4, the $H_2$:oil ratio was lower during selectivation to reduce selectivation time from the 340 hours shown in Example 2. Cases 1 and 2 demonstrate the very high xylenes production that can be achieved with the zeolite-bound catalyst at very reasonable temperatures and low hydrogen:oil ratios. Case 4 shows how an ultra-high selectivity of 95.9% can be achieved at a reasonable conversion and temperature.

EXAMPLE 5

A zeolite bound zeolite catalyst having substantially the same composition as the catalyst described in Example 1 was evaluated for its ability to crack a light cat naphtha feed.

The test was carried out by first steaming the zeolite bound zeolite catalyst at 704° C. for 16 hours for the purpose of aging the catalyst. Next, the naphtha feed was passed over the zeolite bound zeolite catalyst at 650° C., 1.9 hr$^{-1}$ WHSV, and at a 0.85 steam to hydrocarbon ratio. The tests was repeated except that the catalyst comprised MFI bound with 60% by weight of a binder (based on the weight of the catalyst) which comprised silica and alumina.

The results of the tests are shown in Table 3 below:

TABLE 3

| Catalyst | Conventional MFI | Zeolite-Bound MFI |
|---|---|---|
| Conversion | 95.9 | 92.4 |
| Key Product Yields, Wt % | | |
| Ethylene | 26.9 | 31.8 |
| Propylene | 23.2 | 30.3 |
| Butylenes | 7.0 | 6.8 |
| Aromatics | 21.1 | 12.2 |
| Light Saturates | 17.8 | 11.4 |
| Methane | 6.9 | 7.3 |

The results of these tests show that yields of ethylene and propylene were significantly increased and the selectivity to undesirable light saturates and aromatics was significantly reduced using the zeolite bound zeolite as a cracking catalyst.

What is claimed is:

1. A process of isomerizing a hydrocarbon feed containing an aromatic $C_8$ stream comprising ethylbenzene, xylene isomers, or mixtures thereof comprising contacting said feed under isomerization conversion conditions with a zeolite bound zeolite catalyst that does not contain significant amounts of non-zeolitic binder, said catalyst comprising:

(a) first crystals of a first zeolite selected from the group consisting of large pore zeolite and medium pore zeolite having an average particle size greater than about 0.1 micron average particle size; and, (b) a binder comprising second crystals of a second zeolite selected from the group consisting of large pore zeolite and medium pore zeolite having an average particle size less than said first crystals; wherein said second crystals are intergrown and form a coating or partial coating in said first crystals.

2. The process recited in claim 1, wherein said first zeolite is selected from the group consisting of MFI, MEL, MTW, EUO MTT, HEU, FER, TON, ZSM-34, ZSM-38, and ZSM-48.

3. The process recited in claim 2, wherein said second zeolite is selected from the group consisting of MFI, MEL, MTW, EUO, MTT, HEU, FER, TON, ZSM-34, ZSM-38, and ZSM-48.

4. The process recited in 3, wherein said second zeolite has a silica to alumina mole ratio that is greater than the silica to alumina ratio of said first zeolite.

5. The process recited in claim 4, wherein said second zeolite has a silica to alumina mole ratio that is less than the silica to alumina ratio of said first zeolite.

6. The process recited in claim 4, wherein said zeolite bound zeolite catalyst has an Adsorption Index greater than 1.00.

7. The process recited in claim 4, wherein said second zeolite has a silica to alumina mole ratio greater than about 300:1.

8. The process recited in claim 7, wherein said first zeolite has a silica to alumina mole ratio of from about 20:1 to about 150:1.

9. The process recited in claim 8, wherein said second zeolite has a silica to alumina mole ratio greater than 500:1.

10. The process recited in claim 9, wherein said first crystals have a particle size of from about 2 to 6 microns.

11. The process recited in claim 10, wherein said second crystals have a particle size of from about 0.1 to less than 0.5 microns.

12. The process recited in claim 3, wherein said first zeolite and said second zeolite are MFI.

13. The process recited in claim 11, wherein said zeolite bound zeolite catalyst contains less than 10% by weight of non-zeolite binder based on the weight of said first zeolite and said second zeolite.

14. The process recited in claim 13, wherein said first zeolite, said second zeolite or both are gallosilicates or titanosilicates.

15. The process recited in claim 1, wherein first zeolite and said second zeolite are large pore zeolite.

16. The process recited in claim 15, wherein first zeolite is selected from the group consisting of offretite, Beta, and mordenite.

17. The process recited in claim 16, wherein said second zeolite is the same as said first zeolite or a crystallographic match for said first zeolite.

18. The process recited in claim 17, wherein first zeolite and said second zeolite are mordenite.

19. The process recited in claim 11, wherein first zeolite and said second zeolite are medium pore zeolite.

20. The process recited in claim 19, wherein first zeolite and said second zeolite are MFI, MEL, and MTT.

21. The process recited in claim 20, wherein said second zeolite is the same as said first zeolite or a crystallographic match for said zeolite.

22. The process recited in claim 21, wherein first zeolite is gallosilicate.

23. The process recited in claim 21, wherein second zeolite is gallosilicate or silicalite.

24. The process recited in claim 21, wherein first zeolite and said second zeolite are MFI.

25. The process recited in claim 24, wherein said zeolite bound zeolite catalyst contains less than 5% by weight of non-zeolite binder based on the weight of said first zeolite and said second zeolite.

26. The process recited in claim 21, wherein said zeolite bound zeolite catalyst further comprises a Group VIII metal.

27. The process recited in claim 1, wherein said zeolite bound zeolite catalyst further comprises a catalytically active metal.

28. The process recited in claim 27, wherein said catalytically active metal comprises a Group VIII metal.

* * * * *